United States Patent [19]

Di Cristo

[11] Patent Number: 5,318,551
[45] Date of Patent: Jun. 7, 1994

[54] APPLICATOR FOR EXTERNAL URINARY COLLECTION CATHETER

[75] Inventor: Marin Di Cristo, Nice, France

[73] Assignee: Synthelabo, Le Plessis Robinson, France

[21] Appl. No.: 55,563

[22] Filed: May 3, 1993

[30] Foreign Application Priority Data

May 5, 1992 [FR] France .................. 92 05516

[51] Int. Cl.⁵ ............................................ A61F 5/44
[52] U.S. Cl. ................................. 604/349; 128/844
[58] Field of Search ............... 604/347, 349; 128/844

[56] References Cited

U.S. PATENT DOCUMENTS

| | | | |
|---|---|---|---|
| 2,789,560 | 4/1957 | Weimer | 604/349 |
| 4,540,409 | 9/1985 | Nystrom et al. | 604/349 |
| 4,589,874 | 5/1986 | Riedel et al. | 604/349 |
| 4,784,655 | 11/1988 | Campion et al. | 604/349 |
| 4,840,187 | 6/1989 | Brazier | 604/349 |
| 5,211,640 | 5/1993 | Wendler | 604/349 |

FOREIGN PATENT DOCUMENTS 0284224  9/1988  European Pat. Off. .

OTHER PUBLICATIONS

WO 88/02624 International, published Apr. 21, 1988.

*Primary Examiner*—John G. Weiss
*Attorney, Agent, or Firm*—Fisher, Christen & Sabol

[57] ABSTRACT

An applicator for an external urinary collection catheter. The catheter has a flexible sheath intended to be applied in a leaktight manner onto the penis of a patient. The sheath is connected to a tubular shaped part (for receiving the glans) which itself is connected to a tube for removing urine. The sheath is rolled on itself prior to its application. The applicator has a tubular body intended to surround, at least partially, the part for receiving the glans. The body has at least two controllable jaws. One end of each of the jaws is integral with an annular support, and the other free end of each of the jaws has a radially internal projection intended to hook behind the glans and to hold the latter during the unrolling of the flexible sheath on the penis.

10 Claims, 4 Drawing Sheets

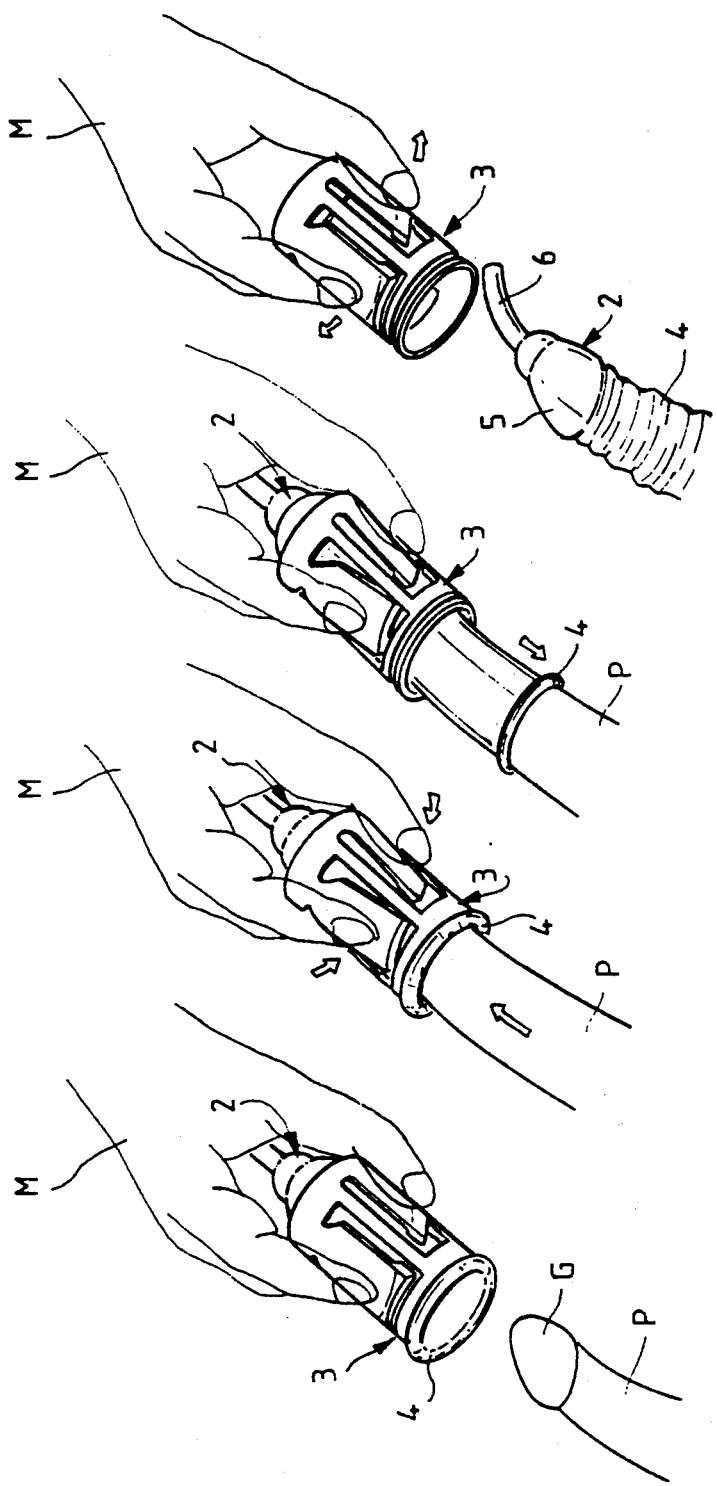

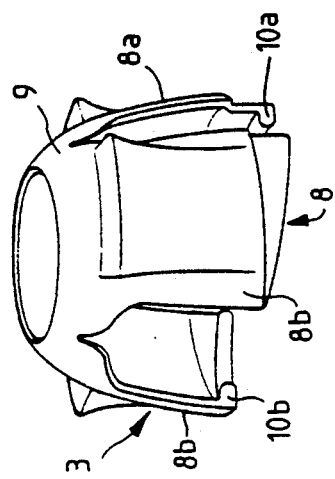
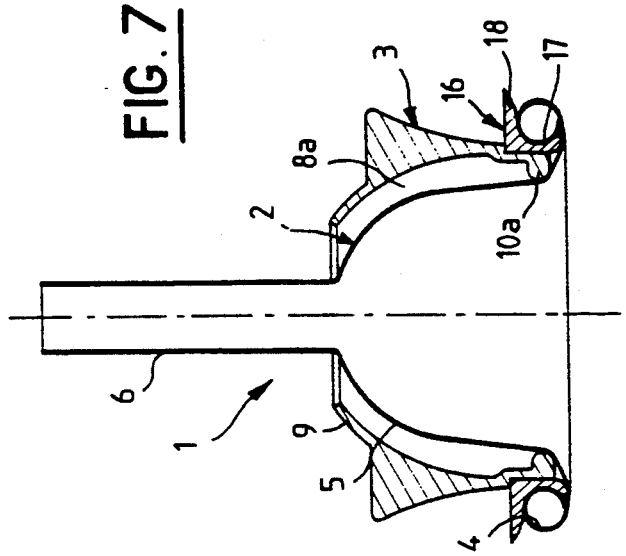
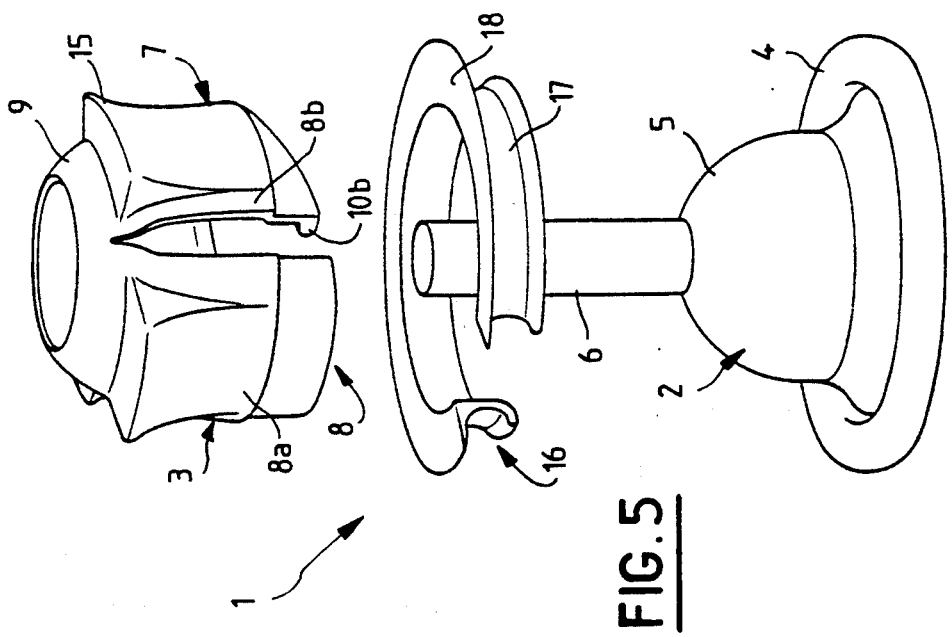

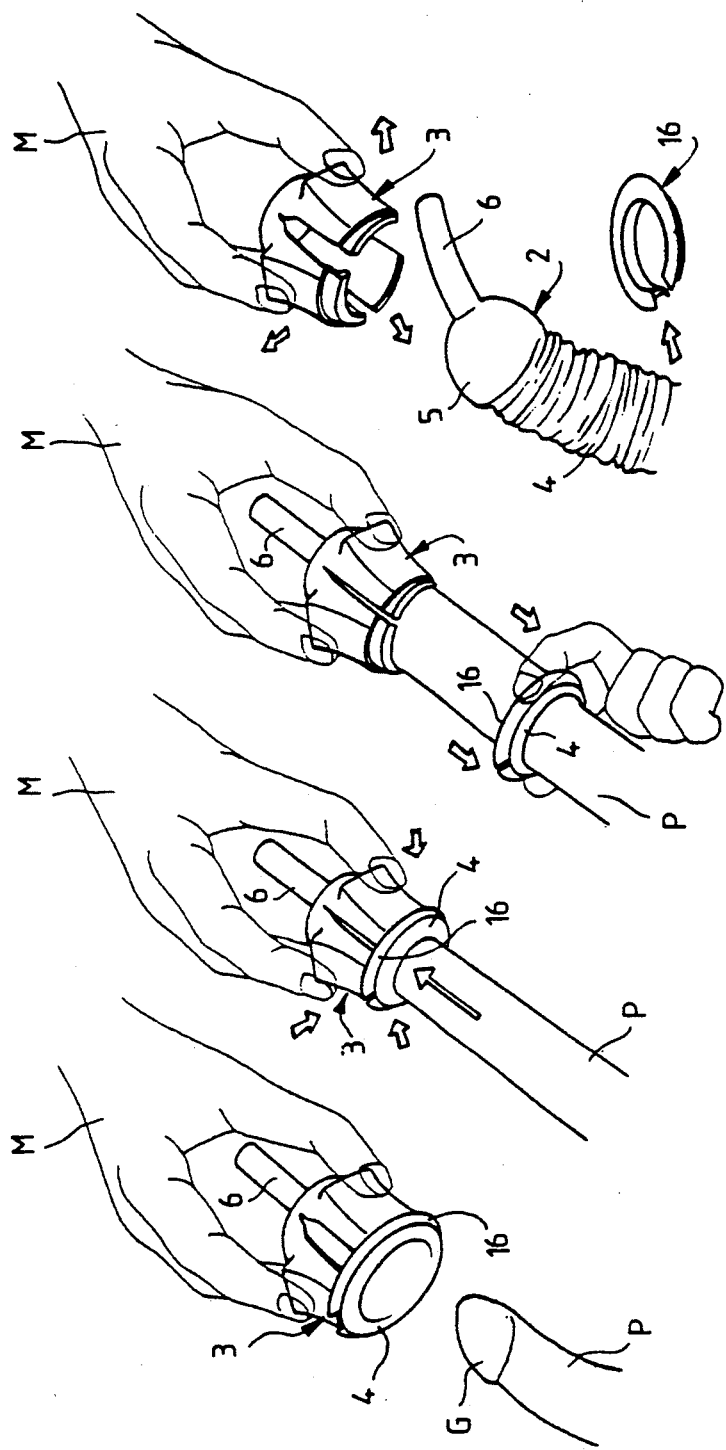

APPLICATOR FOR EXTERNAL URINARY COLLECTION CATHETER

BACKGROUND OF THE INVENTION

1. Field of the Invention

The present invention relates to an applicator for an external urinary collection device comprising individuals, and to a urinary collection device comprising said applicator.

2. Background Art

Urinary collection devices, which are essentially external catheters, are comprised of a flexible sheath intended to be applied in a leaktight manner onto the penis of a patient. The sheath is connected to a part for receiving the glans, substantially in the form of a spherical cap, itself connected to a tube for removing urine, said sheath being rolled on itself prior to its application. It is difficulty to fit such a catheter due to the lack of rigidity of the penis generally exhibited by the patient at the moment of application of the catheter. In order to fit the latter, it is therefore necessary to use an applicator. A catheter/applicator assembly is described, in particular, in U.S. Pat. No. 4,589,874. In this case, the applicator consists of a tubular body intended to partially surround the part for receiving the glans. It has an enlargement behind which the sheath is held in the rolled-up position, making it possible to avoid involuntary unrolling of said sheath. Furthermore, the body has recesses which, during fitting of the catheter, act as openings for the fingers of the operator to grip the part for receiving the glans, and the end of the latter, while, with the other hand, the operator unrolls the sheath. However, under these circumstances, a retraction of the penis is often observed. This prevents the fitting of such a catheter, despite the use of an applicator, such as, the one described in U.S. Pat. No. 4,589,874.

3. Broad Description of the Invention

The object of the present invention is to avoid the above-stated drawback. It relates to an applicator for an external urinary collection catheter which is adapted in order to hold, in a positive manner, the penis and to prevent it from retracting during fitting of the catheter.

For this purpose, the applicator for an external urinary collection catheter, which comprises a flexible sheath intended to be applied in a leaktight manner onto the penis of a patient. The sheath is connected to a part, for receiving the glans, of tubular shape, itself connected to a tube for removing urine, said sheath being rolled on itself prior to its application. The applicator which comprises a tubular body intended to surround, at least partially, said part for receiving the glans, is noteworthy, according to the invention, in that said body comprises at least two controllable jaws, one end of each of which is integral with an annular support, and the other free end of which has a radially internal projection intended to hook behind the glans and to hold the latter during the unrolling of the flexible sheath on the penis.

Thus, by gripping the glans, between the jaws, the operator may pull the virga causing it to extend and thereby facilitate the unrolling of the sheath onto it.

Advantageously, the applicator comprises three jaws, namely a central jaw intended to be applied behind the upper face of the glans, and two lateral jaws located on either side, respectively, of the central jaw.

Preferably, the free ends of the two lateral jaws are bevelled so as to correspond to the anatomical shape of the lateral parts of the glans behind which they are to hook.

In particular, the radially internal projection of the central jaw may be internally rounded.

Furthermore, according to a first embodiment of the invention, the body of said applicator has a general cylindrical shape, and connection tabs are provided between each of said jaws, joining said annular support to a ring fitted with an external groove for receiving the sheath in the rolled-up position.

In this case, each of the connection tabs advantageously has, in the vicinity of said ring, an internal thickening in the extension of the radially internal projections of the jaws, so that the projections/thickenings of the tabs assembly has a shape which corresponds to the anatomical shape of the glans.

According to another embodiment of the invention, the body of said applicator has the general shape of a spherical cap, and, on the external face of each of said jaws, a gripping part is provided which tapers into the shape of a wedge towards the free end of the jaw.

In the latter, the applicator which is in the vicinity of the free ends of the jaws, is preferably comprised of a ring. The ring can be detached from said jaws when the latter are pressed towards each other and comprises a groove for receiving the sheath in the rolled-up position.

Advantageously, said ring comprises a lip for supporting the sleeve, facilitating its unrolling.

BRIEF DESCRIPTION OF THE DRAWINGS

The FIGURES of the attached drawing will exhibit how the invention may be embodied. In these FIGURES, identical references designate similar elements.

FIGS. 4a-4d illustrate different steps in the fitting of the external urinary collection catheter, according to FIGS. 1 to 3, onto the penis of the patient.

FIG. 5 is an exploded perspective view of a second embodiment of the urinary collection device according to the invention.

FIG. 6 is a perspective view of the applicator of the urinary collection device in FIG. 5 from a different angle.

FIG. 7 is a sectional view of the device in FIG. 5 with the applicator in place.

FIGS. 8a-8d illustrate different steps in the fitting of the external urinary collection catheter according to FIGS. 5 to 7, onto the penis of a patient.

DETAILED DESCRIPTION OF THE INVENTION

Figure 3:
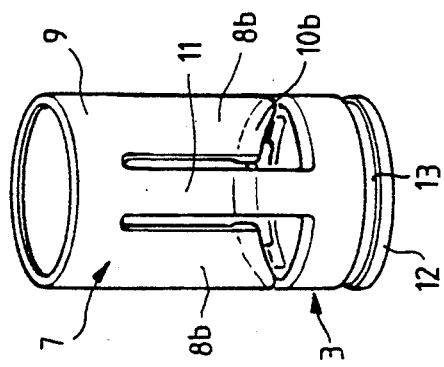
FIGS. 2 and 3 are perspective views, rotated with respect to each other through 180°, of the applicator of the urinary collection device in FIG. 1.0
Figure 2:
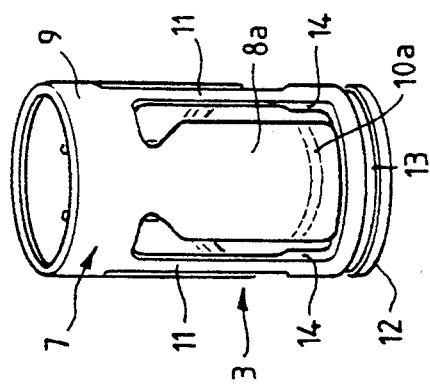
Figure 1:
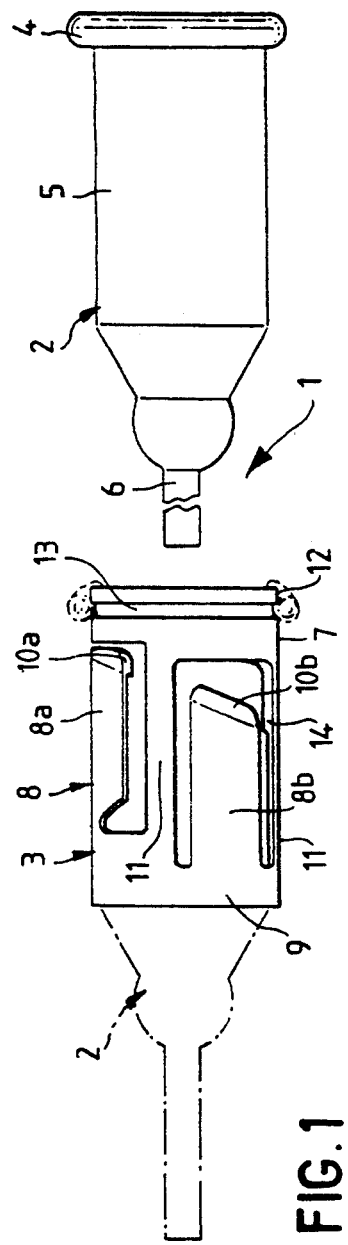
FIG. 1 is an exploded perspective view of a first embodiment of the urinary collection device according to the invention.

As seen in FIGS. 1 to 3, a first embodiment of the urinary collection device 1 is comprised of an external catheter 2 and an applicator 3. In order to clarify the drawing, FIG. 1 shows the catheter 2 (in solid lines) separated from the applicator 3, and the catheter 2 (in broken lines) when the applicator 3 is installed thereon. The catheter 2 comprises a flexible sheath 4, as shown in FIG. 1 in a position rolled on itself, and as intended to be applied onto the penis of a patient, which sheath 4 is connected to a part 5, for receiving the glans, of cylindrical shape, itself connected to a tube 6 for removing urine (which may be connected to means for collecting urine, which are not shown).

Furthermore, the applicator 3 comprises a tubular body 7 of cylindrical shape intended to surround the part 5 for receiving the glans, and comprises a set 8 of three controllable jaws 8a, 8b, 8b. Among the latter, a central jaw 8a is intended to be applied behind the upper face of the glans, and the two lateral jaws 8b, 8b, located on either side, respectively, of the central jaw 8a, are intended to hook behind the lateral parts of the glans. One end of each of the jaws 8a, 8b, 8b is integral with an annular support 9, while the other free end has a radially internal projection 10a, 10b, 10b, each of said projections being intended to hook behind the glans and to hold the latter during the unrolling of the sheath 4 on the penis. For this purpose, the free ends of the two lateral jaws 8b, 8b are bevelled so as to correspond to the anatomical shape of the lateral parts of the glans, while the radially internal projection 10a of the central jaw 8a is internally rounded.

Furthermore, connection tabs 11 are provided between each of the jaws 8a, 8b, 8b, joining the annular support 9 to a ring 12 fitted with an external groove 13 for receiving the sheath 4 in the rolled-up position (in broken lines in FIG. 1). The connection tabs 11 each have, in the vicinity of the ring 12, an internal thickening 14 in the extension of the radially internal projections 10a, 10b, 10b of the jaws 8a, 8b, 8b, so, that the projections/thickenings of the tabs assembly have a shape which corresponds to the anatomical shape of the glans.

FIGS. 4a–4d show the fitting of the external urinary collection catheter 2 onto the penis P of a patient. The device 1 being in the mounted position shown (in broken lines in FIG. 1,) that is to say with the applicator 3 in place on the catheter 2 and the sheath 4 of the latter housed in the groove 13 of the ring 12, the hand M of the operator grasps, with three fingers, the three jaws 8a, 8b, 8b of the applicator (FIG. 4a), when the glans G of the penis P is in position in the part 5 for receiving the catheter 2 (FIG. 4b), the operator, by pressing on the jaws, and by virtue of the radially internal projections 10a, 10b, 10b of the latter, can hook the applicator behind the glans, and, thus, pull on the virga of the patient, avoiding the retraction of the latter, while unrolling the sheath 4 on the penis (FIG. 4c). When the sheath 4 is completely unrolled (FIG. 4d), the catheter 2 is in place, and the operator, by relaxing the pressure on the jaws, can retract the applicator 3.

The second embodiment of the urinary collection device 1, shown in FIGS. 5 to 7, comprises, as in the first embodiment, an external catheter 2 and an applicator 3. The catheter 2 further comprises a flexible sheath 4, connected to a part 5 for receiving the glans, of frustoconical shape, itself connected to a tube 6 for removing urine.

Furthermore, the applicator 3 comprises a body 7 substantially in the shape of a spherical cap, intended to surround the part 5 for receiving the glans, and comprises a set 8 of three controllable jaws 8a, 8b, 8b. As in the preceding embodiment, a central jaw 8a is intended to be applied behind the upper face of the glans, and the two lateral jaws 8b, 8b, located on either side, respectively, of the central jaw 8a, are intended to hook behind the lateral parts of the glans. One end of each of the jaws 8a, 8b, 8b is integral with an annular support 9, while the other free end has a radially internal projection 10a, 10b, 10b, each of said projections being intended to hook behind the glans and to hold the latter during the unrolling of the sheath 4 on the penis. For this purpose, the free ends of the two lateral jaws 8b, 8b are bevelled so as to correspond to the anatomical shape of the lateral parts of the glans, while the radially internal projection 10a of the central jaw 8a is internally rounded.

Furthermore, on the external face of each of the jaws 8a, 8b, 8b, a gripping part 15 is provided which tapers into the shape of a towards the free end of the jaw 8a, 8b, 8b, and facilitates the pulling of the virga during use of the applicator. Furthermore, the applicator comprises, in the vicinity of the free ends of the jaws, a ring 16, which can be detached from the jaws when the latter are pressed towards each other, and which comprises a groove 17 for receiving the sheath 4 in the rolled-up position, as well as a lip 18 for supporting the sheath, facilitating its unrolling.

The fitting of the external urinary collection catheter, in this embodiment of the device, is almost the same as the first embodiment, and is illustrated by the FIGS. 8a–8d. It will be noted, however, that in this case, the ring 16, detached from the jaws of the applicator 3 when these jaws are pressed, is used for unrolling sheath 4 (FIG. 8c).

What is claimed is:

1. An applicator for an external urinary collection catheter, said catheter (2) comprising a flexible sheath (4) intended to be applied in a leaktight manner onto the penis of a patient, which sheath (4) is connected to a tubular shaped part (5), for receiving the glans, said part (5) being connected to a tube (6) for removing urine, said sheath (4) being rolled on itself prior to its application, said applicator (3) comprising a tubular body (7) intended to surround, at least partially, said part (5) for receiving the glans, wherein said body (7) comprises at least two controllable jaws (8a, 8b), each of the controllable jaws (8a, 8b) has two ends with one of said ends being free, the free end of each of the controllable jaws (8a, 8b) has a radially internal projection (10a, 10b) intended to hook behind the glans and to hold the glans during the unrolling of the flexible sheath (4) on the penis, and the other end of each of the controllable jaws (8a, 8b) being integral with an annular support (9).

2. The applicator as claimed in claim 1 wherein said body (7) comprises three jaws (8a, 8b, 8b), of which a central jaw (8a) is intended to be applied behind the upper face of the glans, and two lateral jaws (8b, 8b), are arranged on either side, respectively, of the central jaw (8a).

3. The applicator as claimed in claim 2 wherein the free end of each of the two lateral jaws (8b, 8b) is bevelled so as to correspond to the anatomical shape of the lateral parts of the glans behind which the free end of each of the two lateral jaws (8b, 8b) is to be hooked.

4. The applicator as claimed in claim 2 wherein the radially internal projection (10a) of the central jaw (8a) is internally rounded.

5. The applicator as claimed in claim 2 wherein the body (7) of said applicator (3) has a general cylindrical shape, and connection tabs (11) are provided between each of said jaws, joining said annular support (9) to a ring (12) fitted with an external groove (13) for receiving the sheath (4) in the rolled-up position.

6. The applicator as claimed in claim 5 wherein said jaws each having radially internal projections which each have extension portions, and the connection tabs

(11) each have, in the vicinity of said ring (12), an internal thickening (14) in the extension of the radially internal projections of the jaws, so that the projections and the internal thickenings of the tabs have a shape corresponding to the anatomical shape of glans.

7. The applicator as claimed in claim 1 wherein the body (7) of said applicator (3) has a general shape of a spherical cap, each of said jaws has an external surface and an internal surface, and, on the external face of each of said jaws, a gripping part (15) is provided, tapering into the shape of a wedge towards the free end of the jaw.

8. The applicator as claimed in claim 7 wherein it comprises, in the vicinity of the free ends of the jaws, a ring (16), which can be detached from said jaws when said jaws are pressed towards each other, and which comprises a groove (17) for receiving the sheath (4) in the rolled-up position.

9. The applicator as claimed in claim 8 wherein said ring (16) comprises a lip (18) for supporting the sheath (4) facilitating its unrolling.

10. A urinary collection device comprising (A) an external catheter (2) which comprises a flexible sheath (4) intended to be applied in a leaktight manner onto the penis of a patient, which sheath (4) is connected to a tubular shaped part (5), for receiving the glans, said part (5) being connected to a tube (6) for removal of urine, said sheath (4) being rolled on itself prior to its application, an applicator (3) as defined, and (B) said applicator (3) comprising a tubular body (7) intended to surround, at least partially, said part (5) for receiving the glans, wherein said body (7) comprises at least two controllable jaws (8a, 8b), each of the controllable jaws (8a, 8b) has two ends with one of said ends being free, the free end of each of the controllable jaws (8a, 8b) has a radially internal projection (10a, 10b) intended to hook behind the glans and to hold the glans during the unrolling of the flexible sheath (4) on the penis, and the other end of each of the controllable jaws (8a, 8b) being integral with an annular support (a).

* * * * *